United States Patent
Morton et al.

(10) Patent No.: US 6,558,650 B1
(45) Date of Patent: May 6, 2003

(54) ENHANCEMENT OF CELLULAR GALLIUM UPTAKE

(75) Inventors: Kathryn A. Morton, Portland, OR (US); Jean-Baptiste Roullet, Portland, OR (US)

(73) Assignee: Oregon Health and Science University, Portland, OR (US)

( * ) Notice: Subject to any disclaimer, the term of this patent is extended or adjusted under 35 U.S.C. 154(b) by 0 days.

(21) Appl. No.: 09/647,954

(22) PCT Filed: Apr. 8, 1999

(86) PCT No.: PCT/US99/07879

§ 371 (c)(1),
(2), (4) Date: Oct. 6, 2000

(87) PCT Pub. No.: WO99/51277

PCT Pub. Date: Oct. 14, 1999

Related U.S. Application Data
(60) Provisional application No. 60/081,336, filed on Apr. 8, 1998.

(51) Int. Cl.[7] .............................................. A61K 49/00
(52) U.S. Cl. ...................... 424/9.1; 424/1.11; 424/1.65; 424/9.2; 546/249
(58) Field of Search .............................. 424/1.11, 1.65, 424/9.1, 9.2, 9.3, 9.4, 9.5, 9.6; 530/386; 546/249

(56) References Cited

U.S. PATENT DOCUMENTS

| | | | |
|---|---|---|---|
| 4,448,762 A | 5/1984 | Richards et al. | |
| 4,448,763 A | 5/1984 | Triplett | |
| 5,524,622 A | 6/1996 | Wilson | |

OTHER PUBLICATIONS

Berson et al., "Studies on Dihydropyridines. II. The Photochemical Disproportionation of 4–(2'–Nitrophenyl)–1,4–dihydropyridines[1]," 77:447–450, Jan. 20, 1955.

Jakobsen et al., "Gas Chromatographic Determination of Nifedipine and One of its Metabolites Using Electron Capture Detection," *Journal of Chromatography*, 162:81–87, 1979.

Majeed et al., "Spectrophotometric Study of the Photodecomposition Kinetics of Nifedipine," *J. Pharm. Pharmacol.*, 39:1044–1046, 1987.

Chitambar et al., "Uptake of Gallium–67 by Human Leukemic Cells: Demonstration of Transferrin Receptor–dependent and Transferrin–independent Mechanisms," *Cancer Research*, 47:3929–3934, Aug. 1, 1987.

Kaplan et al., "Regulation of the Transferrin–independent Iron Transport System in Cultured Cells," *The Journal of Biological Chemistry*, 266:2997–3004, Feb. 15, 1991.

Chitambar et al., "Regulatory Effects of Gallium on Transferrin–Independent Iron Uptake by Human Leukemic HL60 Cells," *Blood*, 80:505–511, Jul. 15, 1992.

Grundy et al., "Photostability Determination of Commercially Available Nifedipine Oral Dosage Formulations," *Journal of Pharmaceutical & Biomedical Analysis*, 12:1529–1535, 1994.

Grundy et al., "Sensitive High–performance Liquid Chromatographic Assay for Nifedipine in Human Plasma Utilizing Ultraviolet Detection," *Journal of Chromotagraphy B*, 654:146–151, 1994.

Hayase et al., "Newly Discovered Photodegradation Products of Nifedipine in Hospital Prescriptions," *Journal of Pharmaceutical Sciences*, 83:532–537, Apr. 4, 1994.

Jonkhoff et al. "High–dose Gallium–67 Therapy in Patients with Relapsed Acute Leukaemia: A Feasability Study," *British Journal of Cancer*, 72:1541–1546, 1995.

Hayase et al. "Effects of Photodegradation Products of Nifedipine: The Nitrosoderivative Relaxes Contractions of the Rat Aortic Strip Induced by Norepinephrine and Other Agonists," *The Journal of Pharmacology and Experimental Therapeutics*, 275:813–821, 1995.

(List continued on next page.)

*Primary Examiner*—Dameron L. Jones
(74) *Attorney, Agent, or Firm*—Klarquist Sparkman, LLP

(57) ABSTRACT

A method for improving cellular gallium uptake (particularly of tumor cells) by exposing cells to a nifedipine photodegradation product, or an analog thereof. In particular embodiments, the gallium uptake enhancer is selected from the group of A-B and formula (I), wherein A is a pyridine and B is a nitrosophenyl, and n=1–10. In yet other embodiments, the uptake enhancer is formula (II), wherein $R_{1-9}$ are independently selected from the group consisting of H, halogen, haloalkyl, $NO_2$, NO, $SO_2$, a C1-6 alkyl, a $COOR_{10}$ wherein $R_{10}$ is H or C1-6 alkyl, and an $-OR_{11}$ wherein $R_{11}$ is H or C1-6 alkyl; wherein at least one of $R_5$ and $R_7$ is NO. The uptake enhancers are particularly useful in imaging tumors, using such techniques as gallium scanning, in which the dose of the gallium isotope can be decreased or its imaging efficiency improved. Alternatively, the method can be used to improve efficacy of gallium containing chemotherapeutic regiments in the treatment of tumors and hypercalcemia, or to improve the uptake of other chemotherapeutics that use a similar transferrin independent uptake mechanism.

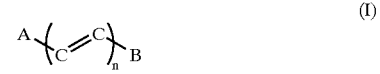

(I)

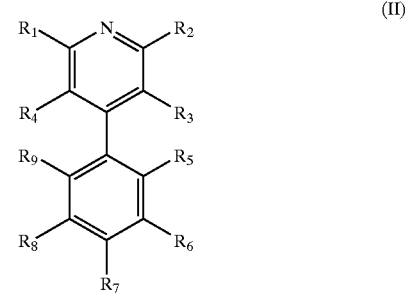

(II)

51 Claims, 3 Drawing Sheets

OTHER PUBLICATIONS

Savigni et al., "Mediation of Iron Uptake and Release in Erythroid Cells by Photodegradation Products of Nifedipine," *Biochemical Pharmacology*, 51:1701–1709, 1996.

van Leeuwen–Stok et al., "Effect of Modulation of the Transferrin Receptor on Gallium–67 Uptake and Cytotoxicity in Lymphoma Cell Lines," *Br J Cancer*, 74(4):619–624, Aug. 1996.

Chitambar et al., "Evaluation of Continuous–Infusion Gallium Nitrate and Hydoroxyurea in Combination for the Treatment of Refractory Non–Hodgkin's Lymphoma," *Am J Clin Oncol*, 20(2):173–178, 1997.

Shukla et al., "Advanced Prostate Cancer Diagnostic and Therapy with Gallium–67 and Yttrium–90, Respectively," *Anticancer Research*, 17:1731–1734, 1997.

Dixon et al., "In vitro Effect of Gallium Nitrate when Combined with Ketoconazole in the Prostate Cancer Cell Line PC-3," *Cancer Letters*, 113:111–116, 1997.

Front et al., "The Continuing Clinical Role of Gallium 67 Scintigraphy in the Age of Receptor Imaging," *Seminars in Nuclear Medicine*, 27:68–74, Jan. 1997.

Dreicer et al., "Vinblastine, Ifosfamide, and Gallium Nitrate—An Active New Regimen in Patients with Advanced Carcinoma of the Urothelium," *American Cancer Society*, 79:110–114, Jan. 1, 1997.

Warrell, "Gallium Nitrate for the Treatment of Bone Metastases," *American Cancer Society*, 80(8):1680–1685, Oct. 15, 1997.

Draisma et al., "Gallium–67 as a Tumor–Seeking Agent in Lymphomas—A Review," *Tumori*, 84:434–441, 1998.

Sandler et al., "Paclitacel Plus Gallium Nitrate and Filgrastim in Patients with Refractory Malignancies," *Am J Clin Oncol*, 21(2):180–184, 1998.

Dreicer et al., "Vinblastine, Ifosfamide, Gallium Nitrate, and Filgrastim in Platinum–and Paclitaxel–Resistant Ovarian Cancer," *Am J Clin Oncol*, 21(3):287–290, 1998.

Luttropp et al., "Uptake of Gallium–67 in Transfected Cells and Tumors Absent or Enriched in the Tranferrin Receptor," *The Journal of Nuclear Medicine*, 39(8):1405–1411, Aug. 1998.

Luttropp et al., "Photodegraded Nifedipine Promotes Transferrin–Independent Gallium Uptake by Cultured Tumor Cells," *J Nucl Med*, 40:159–165, 1999.

Hoffer, "Gallium: Mechanisms," *J Nucl Med* 21:282–285, 1980.

Hayes et al., "Studies of the In Vivo Entry of Ga–67 into Normal and Malignant Tissue," *J Nucl Med* 22:325–332, 1981.

Sohn et al., "Transferrin–Dependent and Independent Uptake of Fe–59 and Ga–67 in Transformed and Untransformed Cells," *J Nucl Med* 34:220, 1993.

Nimodipine

BAY K 8644

FIG. 4

Effect of PDN on Uptake of Ga-67 (various tumor types)

| Histologic Type of Cell/Tumor | Name of Cell | Species/Strain of Origin | *Ga-67 Uptake (SEM1) | *PDN Ga-67 Uptake (SEM) |
|---|---|---|---|---|
| Embryonic sarcoma | MMSV/3T3 | Mouse Balb/C | .062 (.001) | 383.45 (11.09) |
| Myeloma | XS63 | Mouse Balb/C | .149 (.003) | 111.62 (12.70) |
| Renal adenocarcinoma | RAG | Mouse Balb/C | .402 (.010) | 201.34 (15.83) |
| Testicular tumor (leydig cell) | I-10 | Mouse Balb/C | .322 (.007) | 185.61 (12.16) |
| Lymphoma T-cell | RAW 8.1 | Mouse Balb/C | .175 (.018) | 224.53 (8.57) |
| Medullary thyroid | MTC-M | Mouse Balb/C | .333 (.051) | 299.54 (12.54) |
| Neuroblastoma | Neuro 2-A | Rat | .297 (.039) | 138.45 (16.09) |
| Melanoma | HT-144 | Human | .591 (.177) | 343.45 (9.51) |
| Colon adenocarcinoma | Caco-2 | Human | .420 (.035) | 355.01 (13.79) |
| Lung adenocarcinoma | Calu-1 | Human | 1.002 (.513) | 422.67 (17.21) |
| Intraductal breast carcinoma | BT-474 | Human | .518 (.068) | 286.24 (7.77) |

*fmoles Ga/mg total cellular protein
PDN incubated with cells for 30 minutes at concentration of 25 μm

ENHANCEMENT OF CELLULAR GALLIUM UPTAKE

PRIORITY

This patent was filed under 35 U.S.C. § 371 and claims priority from Patent Cooperation Treaty (PCT) International Patent Application PCT/US99/07879, filed Apr. 8, 1999, which in turn claims priority from U.S. Provisional Patent Application 60/081,336, filed Apr. 8, 1998. Both priority applications are incorporated herein by reference.

FIELD OF THE INVENTION

This invention relates to increasing the uptake of gallium into cells for diagnostic and therapeutic purposes.

BACKGROUND OF THE INVENTION

Gallium (Ga), a Group IIIa transition metal, has a number of isotopes with many medical uses. For decades, gallium-67, a gamma-emitter, has been used in nuclear medicine for tumor imaging by gamma emission scintigraphy (1). Currently, gallium-67 is most widely used in staging and assessing the therapeutic response of lymphomas (2, 3, 4, 5). Other isotopes of gallium have potential uses in oncology. Gallium-68, a positron emitter, can be used for tumor imaging by positron emission tomography (PET). Gallium-72, a beta-emitter, may destroy tissues that concentrate gallium by local radiation. This treatment has been proposed to palliate bone pain caused by skeletal metastases (6). Gallium-67 has also been used for local radiotherapy in the treatment of hematological malignancies (48, 49, 50, 51).

Stable (non-radioactive) gallium has been used to reduce the hypercalcemia of malignancy, and as a treatment for Paget's disease of bone. It is also believed to have direct anti-neoplastic effects, and is currently under investigation as an adjunct to conventional chemotherapy (7, 8, 9).

The limitations of Ga-67 for oncologic imaging are well-recognized (10,11,12,13). Many tumors accumulate Ga poorly. Others, such as hepatomas and lymphomas, can be intensely Ga-avid but may vary in magnitude and consistency of uptake. Delineation of tumors from background tissues often requires extended intervals from the time of injection to imaging of 3–7 days or more because Ga-67 localizes slowly and initial images of the abdomen are frequently difficult to interpret because of bowel activity. Because of the extended intervals required for oncologic imaging, a relatively high dose of Ga-67 is required (typically 10 mCi for an adult). Despite its drawbacks, no other gamma-emitting radiopharmaceutical used for tumor imaging in nuclear medicine (including expensive monoclonal antibodies and receptor-avid peptides) has surpassed Ga-67 in cost-effectiveness, general availability, broad applicability and ease of imaging. Although efforts to improve the use of gallium are clearly justifiable, the techniques to accomplish this have thus far been elusive for impractical.

Despite years of imaging experience with the Ga-67 radiometal, the mechanism by which Ga-67 accumulates in normal tissues and tumors remains controversial. For years, it has been thought that gallium is taken up by cells as a gallium-transferrin (Ga-Tf) complex via the transferrin receptor (TfR) (14,15,16). However, there is also evidence that mechanisms other than the TfR may be responsible for the uptake of Ga-67 in tumors (17,18,19). For example, gallium may dissociate from Tf in the acidic extracellular environment of tumors, which would interfere with Tf mediated transport of cellular uptake (20, 21, 22). There is also a poor correlation between TfR density and the degree of tumor uptake of gallium. Moreover, gallium uptake continues to a significant degree even in the absence of Tf, or when TfR binding sites are blocked with an antibody or when iron overload down regulates TfR expression (23, 24, 25).

Tumor bearing rats that are rendered iron-deficient (which increases TfR's in many tissues) exhibit an increased uptake of Ga-67 in tissue other than tumors (26). When Tf binding sites are saturated with iron or scandium after administration of Ga-67, uptake of gallium in tumors, relative to normal tissues, can actually increase (27, 28). Uptake of Ga-67 by nonosseous tissues and organs is markedly depressed in a hypotransferrinemic strain of mouse, suggesting that uptake of Ga-67 by most soft tissues and organs is a Tf-dependent process (29).

Nifedipine 1 (dimethyl 1,4-dihydro-2,6-dimethyl-4-(2-nitrophenyl)-3,5-pyridinedicarboxylate) is a dihydropyridine calcium channel antagonist, which causes vasodilation and lowering of peripheral vascular resistance. These characteristics make nifedipine useful in the treatment of heart disease and hypertension. This compound, like most 1,4-dihydro-4-(2-nitrophenyl)pyridine derivatives, is very sensitive to light. Photo-degradation of nifedipine has been considered a drawback to its pharmaceutical use, because the photo-degradation products have been thought to lack pharmacological activity. Hence photo-degradation of nifedipine has diligently been avoided by shielding it from the light to prevent loss of its therapeutic properties.

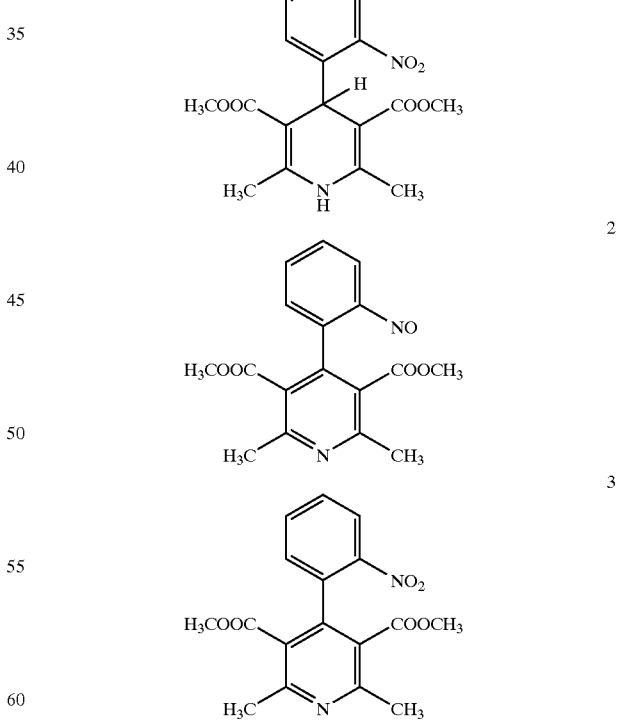

In the presence of light, nifedipine is converted to phenylpyridine derivative structures that include fully-aromatic compounds (FIG. 1). With exposure to visible/fluorescent light, nifedipine is converted predominantly to the 4-(2-nitrosophenyl)pyridine homologue 2 (the nitroso derivative, also known as 2,6-dimethyl-3,5-diacetyl-4-(2'-nitrosophenyl)-pyridine). When exposed to UV light, it is converted predominantly to the 4-(2-nitrophenyl)pyridine homologue 3 (the nitro nifedipine derivative). The nitro derivative is also the primary metabolic product of nifedipine in humans. In addition to these two main structures, photo-degraded nifedipine (PDN) also includes a broad variety of phenylpyridines such as the cis and trans-azoxy derivatives, the hydroxylamine derivative, the amine derivative, the lactam derivative, and the trans-N,N'-dioxide derivative.

SUMMARY OF THE INVENTION

The present invention takes advantage of an unexpected property of nifedipine degradation products, such as photo-degraded nifedipine products (PDN), or pharmaceutical analogs and their degradation products. This property can be used to improve the use of gallium for several purposes: 1) to improve tumor imaging; 2) to improve radiotherapy of tumors; and 3) to improve the use of gallium as an adjunct to chemotherapy. In particular example, the method can improve the uptake of gallium into tumor cells, to permit a total diagnostic or therapeutic dose of the radioisotope to be decreased, so that less than the normal 5–10 mCi adult dose can be administered to an adult.

There are several mechanisms by which PDN can improve the use of gallium isotopes, such as Ga-67 (for gamma scintigraphy), for tumor imaging. First, PDN selectively augments a Tf-independent uptake of gallium, and since tumors appear to accumulate gallium by this route to a greater extent than normal tissues, PDN could improve the localization of gallium selectively in tumors. Even if PDN stimulates uptake of gallium in normal tissues as well as tumors, it still has significant beneficial effect in decreasing the necessary interval between time of injection of the radio-tracer and time of imaging. Improving the efficiency of uptake of gallium in tumors or other tissues allows diagnostic images to be obtained at a lower dose of radioactivity to the patient. Tumor specific enhancement of gallium uptake by PDN improves the use of stable gallium as an adjunct to conventional chemotherapy, and concentration of unstable gallium isotopes in tumors for the purpose of administering local radiotherapy.

The present invention therefore includes exposing cells, tissues or tumors to a sufficient dose of the PDN products, for a sufficient period of time, to improve the uptake of gallium into the cells or tumors. The cells can be exposed to the PDN in vitro (for example is an assay) by providing the photo-degradation products (or biological precursors) in a surrounding medium. Alternatively, the PDN can be administered to cells, tissues or tumors in vivo to achieve a systemic blood level, or a local concentration in a tissue of interest (such as a tumor), sufficient to increase gallium uptake in that tissue. Either the PDN products themselves can be administered, or a biological precursor (such as nifedipine) can be administered and allowed to degrade. The degradation may occur by normal metabolic pathways to one of the photo-degradation products. However, the degradation may alternatively be induced by exposure to light, such as pre-irradiation of a solution of nifedipine prior to its administration, or use of light delivered to the tissue of interest (for example through external or endoscopic fiberoptic light delivery of the kind used in photodynamic therapy).

Nifedipine is well-absorbed orally and achieves peak plasma levels approximately 30 minutes post ingestion. In humans treated with nifedipine, a typical dose range is 0.5–2.0 mg/kg/day, given orally in three equally-divided daily doses. It is anticipated that PDN will be similarly well-tolerated and well-absorbed orally, although it may also prove effective if given by other routes, such as by intravenous, subcutaneous or intramuscular injection. PDN is likely to be effective in a dose range similar to that for nifedipine to achieve a local tissue concentration in the range of 0.25–25 $\mu$M. Even higher tissue concentrations can be used, because the PDNs are relatively otherwise pharmacologically inert. In vitro, cells which are exposed to the PDN compounds in this concentration range for as little as 10 seconds show enhanced gallium uptake.

Any number of the individual PDN structures, such as those shown in FIG. 1, may demonstrate activity in promoting gallium uptake. These particular PDN products can include nitroso-nifedipine, dehydro-nifedipine, the cis or trans-azoxy nifedipine derivative, the trans-N,N'-dioxide nifedipine derivative, the hydroxylamine, amine or lactam derivatives, or any other degradation products of nifedipine or other dihydropyridine that increases the uptake of gallium into cells. The cells which are exposed to these compounds are, for example, tumor cells. However, the method of the present invention can also be used with other cells or tissues in vivo in which concentration of gallium is increased by exposure to nifedipine photo-degradation products.

The invention also includes pharmaceutical compositions of nifedipine photo-degradation products or their precursors, either in isolation or in combination with a pharmaceutical carrier, and in unit dosage forms. All routes of administration of PDN products or their precursors are included in this invention. The invention also includes methods of diagnosis and treatment in which nifedipine (or another 4-phenyldihydropyridine derivative) is intentionally exposed to light (such as visible or ultraviolet light) to produce the photo-degradation products. This intentional exposure can take place either prior to administration of the drug to a subject, or in situ in the body. The period of exposure of the nifedipine to light is for a sufficient period of time to produce an adequate concentration of photo-degradation products, for example at least about 1 minute, or 1 to 5 minutes, or even several hours, for example about 4 hours, or as long as a day or more. This invention also includes pharmaceutical compositions of photo-derivatives of nifedipine that are used to promote gallium uptake, regardless of whether these derivatives are produced by photo-irradiation or by alternate methods, such as chemical synthesis.

In particular embodiments, the invention includes a method of increasing gallium uptake by a cell, by exposing the cell to an effective amount of a gallium uptake enhancer comprising a nifedipine photodegradation product, or an analog thereof, that promotes gallium uptake by the cell. The cells are (simultaneously or substantially concurrently) exposed to a gallium compound such as a salt containing a stable or unstable isotope. The gallium compound may be, for example, gallium nitrate, gallium citrate or gallium chloride. Examples of the gallium metal or isotope are Ga-67, Ga-68, GA-69, Ga-71 and Ga-72 (where Ga-69 and 71 are stable isotopes, and the others are unstable radioactive isotopes).

The cell which is exposed to the gallium and the uptake enhancer may be a tumor cell, so that uptake of chemotherapeutic amounts of gallium into the tumor can be differentially increased, compared to non-tumor cells. The cells can also substantially simultaneously be exposed to adjuvant chemotherapeutic anti-neoplastic pharmaceutical agents, such as vinblastine, ifosfamide, hydroxyurea, paclitaxel, cisplatin, methotrexate, 1-beta-D-arabinofuranosylcytosine, and etoposide. Particular examples of tumor cells which could be exposed to the gallium and uptake enhancer are a sarcoma, myeloma, renal adenocarcinoma, testicular leydig cell tumor, medullary thyroid carcinoma, neuroblastoma, melanoma, colon adenocarcinoma, lung adenocarcinoma, or intraductal breast carcinoma.

In yet other embodiments, the method is used to increase uptake of gallium into bone, for example to treat bone specific conditions such as osteoporosis, or to treat hypercalcemia (such as hypercalcemia caused by hyperparathyroidism or malignancy), or to treat Paget's disease of bone.

The disclosed methods can be used to increase cellular gallium uptake either in vitro or in vivo. For in vivo applications, the gallium and the gallium uptake enhancer are administered to a subject, such as someone who has been diagnosed with a tumor. The gallium may be administered in a therapeutically effective antineoplastic amount, when combined with the gallium uptake enhancer. Alternatively, the gallium may be administered in an amount effective to image the tumor in a gallium scan, when the gallium is administered in combination with the gallium uptake enhancer. Combined administration does not require simultaneous administration, but can refer to simultaneous, substantially simultaneous or separate administration. In particular embodiments, the gallium uptake enhancer is administered prior to the gallium, but within a sufficient period of time to enhance uptake by the tissue of interest (such as the tumor).

Disclosed embodiments of the invention include a gallium uptake enhancer which enhances gallium uptake by a transferrin independent mechanism. Particular examples of such enhancers include a nitrosophenylpyridine, such as the 2'-nitrosophenyl photodegradation product of nifedipine, or a 2'- or 4'-analog thereof. The 2'-nitroso-nifedipine photodegradation product (labeled "nitroso-derivative" in FIG. 1) is believed to be particularly effective in promoting gallium uptake.

In yet other embodiments, the gallium uptake enhancer is selected from the group consisting of:

A-B and

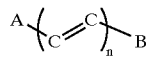

wherein A is a pyridine and B is a nitrosophenyl (such as a 2'-nitrosophenyl or 4'-nitrosophenyl), and n=1–10. Alternatively, the gallium uptake enhancer is:

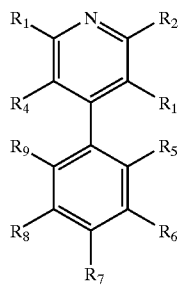

wherein $R_{1-4}$, $R_6$, and $R_{8-9}$ are independently selected from the group consisting of H, halogen (particularly Cl), haloalkyl (particularly $CCl_2$), $NO_2$, NO, $SO_2$, a C1-6 alkyl, a $COOR_{10}$ wherein $R_{10}$ is H or C1-6 alkyl, and an $-OR_{11}$ wherein $R_{11}$ is H or C1-6 alkyl;

and $R_5$ and $R_7$ are independently selected from the group consisting of H, halogen, haloalkyl, $NO_2$, NO, $SO_2$, a C1-6 alkyl, a $COOR_{10}$ wherein $R_{10}$ is H or C1-6 alkyl, and an $-OR_{11}$ wherein $R_{11}$ is H or C1-6 alkyl, wherein at least one of $R_5$ and $R_7$ is NO.

In particular embodiments in which one of $R_5$ and $R_7$ is NO, $R_{1-9}$ are selected from the group of H, a C1-6 alkyl, and $COOR_{10}$, where $R_{10}$ is lower alkyl, such as methyl or ethyl. In some embodiments, R1=R2=lower alkyl such as methyl, and R4=R5=an ester, such as $COOCH_3$. $R_5$ may be NO, and $R_{6-9}$=H.

In particular embodiments, $R_{1-4}$, $R_6$, and $R_{8-9}$ are independently selected from the group consisting of C1-6 alkyl, a $COOR_{10}$ wherein $R_{10}$ is H or C1-6 alkyl, and $-OR_{11}$ wherein $R_{11}$ is H or C1-6 alkyl. In even more particular embodiments, $R_5$ is NO and $R_7$ is H; $R_1$=$R_2$=H, $R_3$=$R_4$=$COOCH_3$; and $R_6$=$R_8$=$R_9$=H.

Even more broadly, the gallium uptake enhancer may be selected from

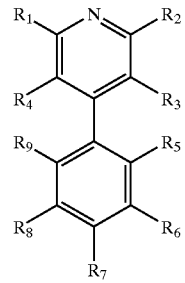

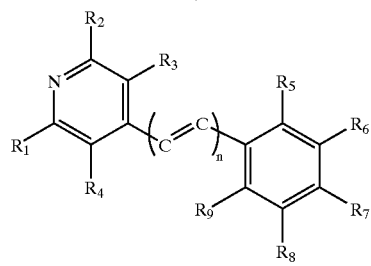

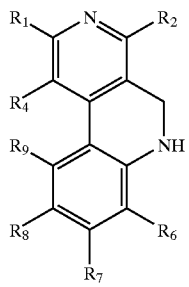

wherein n=1–10, and wherein $R_{1-4}$, $R_6$, and $R_{8-9}$ are independently selected from the group consisting of H, halogen, haloalkyl, $NO_2$, NO, $SO_2$, a C1-6 alkyl, a $COOR_{10}$ wherein $R_{10}$ is H or C1-6 alkyl, and an $-OR_{11}$ wherein $R_{11}$ is H or C1-6 alkyl;

and $R_5$ and $R_7$ are independently selected from the group consisting of H, halogen, haloalkyl, $NO_2$, NO, $SO_2$, a C1-6 alkyl, a $COOR_{10}$ wherein $R_{10}$ is H or C1-6 alkyl, and an $-OR_{11}$ wherein $R_{11}$ is H or C1-6 alkyl, wherein at least one of $R_5$ and $R_7$ is NO.

or wherein $R_{1-4}$, $R_6$, and $R_{8-9}$ are independently selected from the group consisting of H, NO, a C1-6 alkyl, a $COOR_{10}$ wherein $R_{10}$ is H or C1-6 alkyl, and an —$OR_{11}$ wherein $R_{11}$ is H or C1-6 alkyl;

and $R_5$ and $R_7$ are independently selected from the group consisting of H, NO, a C1-6 alkyl, a $COOR_{10}$ wherein $R_{10}$ is H or C1-6 alkyl, and an —$OR_{11}$ wherein $R_{11}$ is H or C1-6 alkyl, wherein at least one of $R_5$ and $R_7$ is NO, particularly $R_5$.

Particular embodiments of the method include imaging a tumor with a gallium scan, by administering to a subject an effective amount of a gallium uptake enhancer, such as a nifedipine photodegradation product, or an analog thereof, that increases uptake of gallium by a tumor. A sufficient amount of gallium is also administered to the subject to perform the gallium scan, wherein the sufficient amount of gallium is less than required to perform the gallium scan in the absence of the gallium uptake enhancer. When the gallium uptake enhancer is a transferrin independent gallium uptake enhancer such as a 2'-nitrosophenylpyridine, transferrin independent uptake selectively concentrates the gallium in the tumor to improve the imaging signal obtained from the tumor. When the method is used to improve imaging of tumors, Ga-67 is a particularly suitable isotope, and 50% or less of the usual dose of 10 millicuries of gallium can be administered to perform the scan. Hence a dose of less than about 5 millicuries of the Ga-67 can be used. The uptake enhancer can also allow the tumor to be imaged much more quickly than in the absence of the enhancer. Hence instead of waiting 36–72 hours to obtain the image, the diagnostic procedure can be performed 24 hours or less after administration of the gallium.

In embodiments in which a nifedipine photodegradation product (such as 2'-nitrosophenylpyridine derivative) is administered to the subject, a dose of about 0.5 to about 2.0 mg/kg/day of the nifedipine photodegradation product may be employed. However, the nifedipine photodegradation products are not known to have any biological effect (other than enhancing gallium uptake). In particular, they do not act as calcium channel antagonists. Hence even much higher doses of nifedipine photodegradation products can be used.

In yet other embodiments in which a cutaneous tumor (such as a melanoma) is to be treated, the gallium uptake enhancer is nifedipine applied to skin in an area of the cutaneous tumor, which area is subsequently irradiated with light (such as visible/fluorescent light) that produces the nifedipine photodegradation product gallium uptake enhancer. However, cutaneous and other types of tumors may also be sensitized by administering the gallium uptake enhancer systemically (for example intravenously or orally) to a subject having the tumor.

The invention also includes methods of screening for a gallium uptake enhancer, by exposing cells to a test agent such as a nifedipine photodegradation product, or an analog thereof, in the presence of gallium. The uptake of gallium in the cell is then measured to determine whether the cellular uptake of gallium is greater or less than in the absence of the test agent. In particular disclosed embodiments, the cells are cultured Chinese Hamster Ovary (CHO) cells, such as transferrin receptor negative CHO cells.

Additional objects and advantages of the present invention will be apparent from the following detailed description of a preferred embodiment, which proceeds with reference to the accompanying figures.

BRIEF DESCRIPTION OF THE DRAWINGS

FIG. 4 is a chart illustrating gallium uptake by tumor cells. A solution of 25 mM nifedipine was exposed to a strong fluorescent light source for 4 hours. The photo-degraded nifedipine was then incubated with tumor cells at a concentration of 25 $\mu$M for 30 minutes in the presence of Ga-67 citrate (PDN Ga-67 uptake). Control tumor cells were incubated in the absence of PDN in the presence of Ga-67 citrate for 30 minutes (Ga-67 uptake).

DETAILED DESCRIPTION OF SEVERAL EMBODIMENTS

Figure 1:
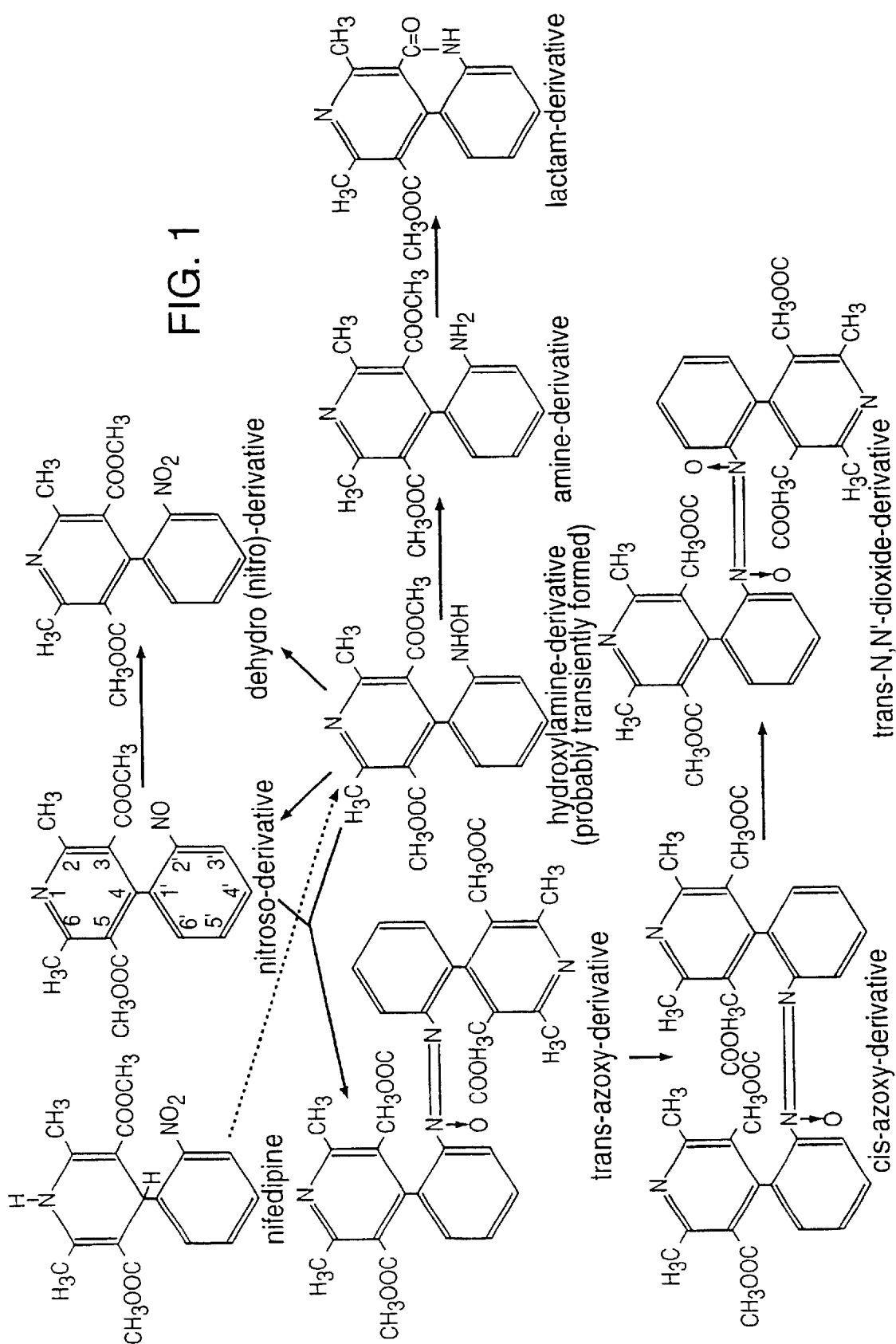
FIG. 1 is a drawing of the degradation pathway of nifedipine, showing examples of nifedipine's many intermediate degradation products. This invention includes, but is not limited to, any of these illustrated structures that enhance gallium uptake, but also includes any chemical or photo-derivative of nifedipine or other dihydropyridines that proves effective in improving the cellular or tissue uptake of gallium.

Abbreviations
  Tf: Transferrin
  TfR: Transferrin receptor
  TfR−: Transferrin receptor negative (lacking a transferrin receptor)
  TfR+: Transferrin receptor positive (having a transferrin receptor)
  PDN: Photo-degraded nifedipine Definitions The following definitions will help with an understanding of the terms used in this specification.

A "gallium uptake enhancer" is an agent that increases the amount of gallium in a cell above the amount that is present in the absence of such a gallium uptake enhancer.

A "transferrin-independent gallium uptake enhancer" is a gallium uptake enhancer that acts by, but is not limited to, a mechanism independent of transferrin. A transferrin-independent gallium uptake enhancer may also increase gallium uptake by a mechanism dependent on transferrin.

"Gallium" includes isotopes of gallium, such as Ga-67, Ga-68, Ga-69, Ga-71, or Ga-72, (where Ga-69 and 71 are stable, and Ga-67, 68, 70 and 72 are unstable), and compounds such as gallium nitrate, gallium citrate, or gallium chloride salts.

A "gallium scan" is a nuclear medicine imaging technique in which a radioactive isotope of gallium, such as Ga-67, is given to a patient intravenously. After administration, the gamma emissions are measured with a gamma camera which produces a photographic image that correlates intensity of tissue uptake with darkness of image. The photographic image provides information that is useful for diagnosis and therapeutic assessment.

A "PET scan" is a nuclear medicine imaging technique in which a radioactive isotope of gallium that emits positrons, such as Ga-68, is administered to a patient intraveneously. After administration, the positron emissions are measured and the information is used for diagnosis and therapeutic assessment.

"Visible light" includes light having a wavelength between about 380–760 nm. "Ultraviolet light" has a wavelength immediately below visible (violet) light, and extends from about 100–380 nm.

A "tumor" is a neoplasm, and includes both benign and malignant tumors. This term particularly includes malignant tumors which can be either solid (such as a breast, liver, or prostate carcinoma) or non-solid (such as a leukemia). Tumors can also be further divided into subtypes, such as adenocarcinomas (e.g. of the breast, prostate or lung).

A "therapeutically effective dose" is a dose sufficient to prevent advancement, or to cause regression of the disease, or which is capable of relieving symptoms caused by the disease.

"Fully-aromatic ring system" is a ring system (such as a phenylpyridine) in which both rings of the system are aromatic.

The term "alkyl" refers to a cyclic, branched, or straight chain alkyl group containing only carbon and hydrogen, and unless otherwise mentioned contains one to twelve carbon atoms. This term is further exemplified by groups such as methyl, ethyl, n-propyl, isobutyl, t-butyl, pentyl, pivalyl, heptyl, adamantyl, and cyclopentyl. Alkyl groups can either be unsubstituted or substituted with one or more substituents, e.g. halogen, alkyl, alkoxy, alkylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality.

The term "lower alkyl" refers to a cyclic, branched or straight chain monovalent alkyl radical of one to six carbon atoms, but can also include up to 3, 4 or 5 carbon atoms. This term is further exemplified by such radicals as methyl, ethyl, n-propyl, i-propyl, n-butyl, t-butyl, i-butyl (or 2-methylpropyl), cyclopropylmethyl, i-amyl, and n-amyl. Lower alkyl groups can also be unsubstituted or substituted, where a specific example of a substituted alkyl is 1,1-dimethyl propyl.

"Hydroxyl" refers to —OH.

"Carboxyl" refers to the radical —COOH, and includes both unsubstituted and substituted carboxyl. "Substituted carboxyl" refers to —COR where R is alkyl, lower alkyl or a carboxylic acid or ester.

The term "aryl" refers to a monovalent unsaturated aromatic carbocyclic group having a single ring (e.g. phenyl) or multiple condensed rings (e.g. naphthyl or anthryl), which can optionally be unsubstituted or substituted with, e.g., halogen, alkoxy, mercapto (—SH), alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

The term "alkoxy" refers to a substituted or unsubstituted alkoxy, where an alkoxy has the structure —O—R, where R is substituted or unsubstituted alkyl. In an unsubstituted alkoxy, the R is an unsubstituted alkyl. The term "substituted alkoxy" refers to a group having the structure —O—R, where R is alkyl which is substituted with a non-interfering substituent.

The term "heterocycle" refers to a monovalent saturated, unsaturated, or aromatic carbocyclic group having a single ring (e.g. benzyl, morpholino, pyridyl or furyl) or multiple condensed rings (e.g. naphthyl, quinolinyl, indolizinyl or benzo[b]thienyl) and having at least one heteroatom, defined as N, O, P, or S, within the ring, which can optionally be unsubstituted or substituted with, e.g. halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

The term "halogen" refers to fluoro, bromo, chloro and iodo substituents.

A "pharmaceutical agent" or "drug" refers to a chemical compound or composition capable of inducing a desired therapeutic or prophylactic effect when properly administered to a subject.

All chemical compounds include both the (+) and (−) stereoisomers, as well as either the (+) or (−) stereoisomer.

An analog is a molecule, that differs in chemical structure from a parent compound, for example a homolog (differing by an increment in the chemical structure, such as a difference in the length of an alkyl chain), a molecular fragment, a structure that differs by one or more functional groups, or a change in ionization. Structural analogs are often found using quantitative structure activity relationships (QSAR), with techniques such as those disclosed in Remington: *The Science and Practice of Pharmacology*, 19$^{th}$ Edition (1995), chapter 28. A derivative is a biologically active molecule derived from the base structure.

Other chemistry terms herein are used according to conventional usage in the art, as exemplified by The McGraw-Hill Dictionary of Chemical Terms (1985) and The Condensed Chemical Dictionary (1981).

A "mammal" includes both human and non-human mammals. Similarly, the term "subject" includes both human and veterinary subjects.

An animal is a living multicellular vertebrate organism, a category which includes, for example, mammals and birds.

The following Examples show that the photo-degradation products of the present method improve gallium uptake in cultured cells, and are intended to illustrate, but not limit, embodiments of the present invention.

EXAMPLE 1

Cell Line and Culture

A pair of transfected Chinese Hamster Ovary cells lines were used to compare, in a controlled manner, the Tf-dependent and Tf-independent systems for the uptake of Ga-67. Details regarding plasmid construction, and the transfection, selection, and characterization of the cells have been recently described (37), and that disclosure is incorporated by reference.

The two cell lines are identical except that TfR-cells express no TfR, and TfR+ cells over-express the transfected human TfR constitutively. This means that expression of the TfR is independent of cell growth or iron content, which could alter the cells matabolically in many ways that may confound a well-controlled experimental determination of cause and effect. TfR− and TfR+ cells were grown in monolayer and maintained as previously described (37).

EXAMPLE 2

Photo-degradation of Nifedipine

Nifedipine (Sigma Chemical Co., St. Louis Mo.) was dissolved in 1 ml ethanol at a concentration of 10 mM. Care was taken to shield nifedipine from the light except during intentional irradiation. For photo-irradiation by fluorescent light, the nifedipine in ethanol was placed in a clear 10 ml polystyrene conical bottom screw cap tube. The tube was placed on its side on the surface of a cool, daylight color-balanced, fluorescent light box (Just Normlicht). For irradiation by UV light, the nifedipine solution was placed in a quartz glass cuvette and placed on the surface of a UV light box (Fotodyne) in an otherwise dark cabinet for 4 hours. The interval of photo-irradiation ranged from 1 minute to 24 hours.

The temperature at the surface of the light box was 29° C. for the fluorescent light box, and 37° C. for the UV light box.

The PDN was added to 10 ml of incubation solution (below) to achieve concentrations ranging from 0.25 µM to 100 µM. Each 10 ml sample of incubation solution contained an equal quantity of ethanol (approximately 100 □l per 10 ml), including the controls.

EXAMPLE 3

Gallium Uptake

Following growth of cells in 25 cm² flasks to subconfluence, monolayers of cultured cells were first washed, and then pre-incubated for 2 hours at 37° C. with 5 ml serum-free Dulbecco's Modified Essential Medium (DMEM) to deplete the cells of Tf. The pre-incubation medium was then removed and replaced by 1.5 ml of the incubation solution containing 10 uCi/ml carrier-free Ga-67 citrate (Mallinckrodt) in Hank's Balanced Salt solution (HBSS), pre-warmed to 37° C. The concentration of Ga-67 in the incubation solution was approximately 0.25 nM. The HBSS, pH 7.2–7.4, contained 3.7 g/L NaHCO3, 1 mM $CaCl_2$, and 1 mM magnesium salts. Cells were incubated in the PDN- and Ga-67-containing solutions in a $CO_2$ incubator at 37° C. for intervals ranging from 10 seconds to 90 minutes. All experiments were conducted in the dark.

Following incubation of cells with Ga-67, the flasks were immediately placed on ice. The radioactive material was removed by aspiration with a Pasteur pipette attached to water suction. The monolayers were washed 3 times with 5 ml each ice cold HBSS. Cells were washed once with phosphate-buffered saline (PBS), pre-warmed to 37° C. The PBS was removed and the cellular monolayer overlaid with 1.5 ml 0.25% trypsin containing 1 mM EDTA. The trypsin was immediately removed and the cells were incubated briefly (1 minute) at 37° C. The cells in each flask were then dislodged by several gentle mechanical blows to the side of the flask and collected in 200 µl ice cold PBS.

By a modification of a method previously published for radiolabeling of protozoan parasites (38), the cells were then separated from unbound contaminating radioactivity. The 200 µl of cells in PBS were layered gently over 200 µl of an 8.5:1.5 ratio of dibutylpthalate:liquid paraffin oil in a 1.5 ml microfuge tube. With care not to agitate the mixture, the tubes were than centrifuged at 12,000 rpm for 2 minutes in a microfuge. The supernatant and the oil was then aspirated carefully from the top of the tube with a Pasteur pipette attached to water suction. The bottom of the microfuge tube, containing the cell pellet (typical pellet volume~100 µl), was then clipped with a microfuge tube clipper into a counting vial containing 900 µl of a solution of 200 mM NaOH. 1% SDS. The cell pellet was dissolved in this solution. The content of radioactivity in the samples was determined by a gamma well counting (Packard) in comparison to standard dilutions of the original Ga-67 incubation solution.

Protein assays were performed on the solubilized cell samples by formation of a cuprous bicinchonicic acid complex using a spectrophotometric microtiter plate reader (Dynatech) (39). The method and reagents used are supplied in a kit (Pierce) and were performed according to the manufacturer's directions.

By photo-irradiation for intervals ranging from 1 minute to 24 hours, the time required for maximal conversion of nifedipine to a form that would promote uptake of Ga-67 was determined (Table 1, below). Nifedipine shielded from the light has no effect on uptake of Ga-67. Exposure to as little as 1 minute of UV or fluorescent light results in a product that stimulates Ga-67 uptake 2–3 fold over basal levels. The same maximal degree of Ga-67 uptake is produced by nifedipine irradiated by UV as by fluorescent light, approximately 1000-fold greater than basal levels. However, there were some differences between the UV and fluorescent effects. Maximal uptake of Ga-67 is produced by 4 hours of fluorescent irradiation of nifedipine, while irradiation for only 1 hour of UV light is required for the maximal effect. There is no loss of activity for nifedipine continuously exposed to fluorescent light for 24 hours. However, continuous exposure of nifedipine to UV light for intervals longer than 1 hour results in progressive diminution of activity.

TABLE 1

Effect of Length of Photo-Irradiation of Nifedipine on Cellular Uptake of Ga-67

| Time of Photo-irradiation of Nifedipine | fmoles Ga-67/mg Total Cellular Protein (SEM) | |
|---|---|---|
| | TfR− cells | TfR+ cells |
| no nifedipine | 0.200 (0.130) | 0.243 (0.009) |
| protected from light | .171 (0.011) | 0.296 (0.013) |
| 1 min | 0.572 (0.105) | 0.644 (0.093) |
| 5 min | 30.339 (2.206) | 25.479 (2.457) |
| 1 h | 141.605 (9.769) | 139.607 (9.710) |
| 4 h | 185.097 (9.913) | 201.249 (9.914) |
| 24 h | 182.199 (12.036) | 196.803 (7.181) |

A solution of 10 mM nifedipine was exposed to a strong fluorescent light source for various lengths of time shown at left. The photo-degraded nifedipine was then incubated with cultured TfR− and TfR+ cells at a concentration of 25 µM for 30 minutes in the presence of Ga-67 citrate.

Stimulation of uptake of Ga-67 by nifedipine irradiated by either UV or fluorescent light is a concentration-dependent phenomenon. Concentration of PDN as low as 0.25 µM result in an uptake of Ga-67 that is 40-fold greater than control levels. Maximal uptake of Ga-67, approximately 1000-fold greater than control levels, is achieved by 25 µM of either the UV or fluorescent-irradiated nifedipine (Table 2). With higher concentrations of nifedipine, no further increase in uptake was observed. With the UV-irradiated product, there is actually a slight but significant decline in activity when the concentration is raised from 25 to 100 µM. Basal and stimulated levels of uptake of Ga-67 are not altered by either pre-incubation of the cells with 100 µM light-shielded nifedipine, or by it's addition to the incubation mixture containing the 25 µM of PDN.

TABLE 2

Effect of Concentration of Photodegraded Nifedipine on Cellular Uptake of Ga-67

| Concentration of Photo-Degraded Nifedipine | fmoles Ga-67/mg Total Cellular Protein (SEM) | |
|---|---|---|
| | TfR− cells | TfR+ cells |
| 0 µM | 0.186 (0.15) | 0.210 (0.018) |
| 0.25 µM | 8.218 (0.855) | 7.525 (1.113) |
| 5 µM | 39.250 (5.514) | 36.608 (3.793) |
| 25 µM | 210.513 (8.255) | 208.101 (13.599) |
| 100 µM | 210.365 (19.276) | 222.554 (11.909) |

A solution of 25 µM nifedipine was exposed to a strong fluorescent light source for 4 hours The photo degraded nifedipine was then incubated at various concentrations with cultured TfR− and TfR+ cells for 30 minutes in the presence of Ga-67 citrate.

Cellular uptake of Ga-67 in the presence of nifedipine degraded by either UV or fluorescent light is very rapid, and does not require pre-incubation with PDN. With even 10 seconds of incubation with Ga-67 in the presence of PDN, uptake of Ga-67 is 6–10 fold greater than basal levels (achieved by cells incubated with Ga-67 alone for 30 minutes). With 30 minutes of exposure to Ga-67 and photo-degraded nifedipine, uptake of Ga-67 is 1000-fold greater than basal levels (Table 3, below).

TABLE 3

Effect of Time of Incubation with Photo-Degraded Nifedipine on Cellular Uptake of Ga-67

| Time of Incubation with Photo-Degraded Nifedipine | fmoles Ga-67/mg Total Cellular Protein (SEM) | |
| --- | --- | --- |
| | TfR− cells | TfR+ cells |
| control (no nifed.) 30 min | 0.186 (0.015) | 0.210 (0.018) |
| 10 sec | 1.784 (0.262) | 1.334 (0.378) |
| 1 min | 6.550 (0.834) | 9.892 (0 989) |
| 5 min | 65.735 (9.428) | 73.506 (8.167) |
| min | 125.463 (6.196) | 117.397 (7.583) |
| 30 min | 181.674 (5.911) | 201.525 (15.837) |
| 90 min | 243.373 (11.794) | 253.843 (8.534) |

A solution of 25 µM nifedipine was exposed to a strong fluorescent light source for 4 hours. The photo degraded nifedipine was then incubated with cultured TfR− and TfR+ cells at a concentration of 25 uM for various intervals in the presence of Ga-67 citrate. The control was incubated in the absence of nifedipine for 30 minutes.

TfR+ and TfR− cells demonstrate equivalent degrees of transferrin-independent uptake of Ga-67 and of stimulation of uptake by PDN. Therefore, the mechanism stimulated by the nifedipine derivatives is unrelated to expression of the TfR, or to any contaminating transferrin in the medium. The TfR− and TfR+ cells, derivatives of CHO cells, are not unique in their enhancement of Ga-67 uptake in response to PDN. Two other lines of cultured cells (Balb/3T3 cells transformed by the Moloney Murine Sarcoma Virus and NIH 3T3 cells, American Type Culture Collection) have also been tested and demonstrate a pattern and magnitude of PDN-stimulated Ga-67 uptake similar to that of the CHO-derived cells.

EXAMPLE 4

Nifedipine Photodegradation Products

The isolation, identification and kinetics of formation of the photo-degradation products of nifedipine have been described (40,41) and some of the known degradation products are shown in FIG. 1. As already noted, these derivatives have previously been considered undesirable because they lack pharmacological activity. Exposure of nifedipine to daylight or fluorescent light results predominantly in the nitroso-derivative degradation product (FIG. 1), which is relatively stable. The other products are either formed only transiently or in small amounts after extended exposure to daylight or fluorescent light (42,43). The dehydro (nitro)-derivative (FIG. 1) is the primary metabolic product of nifedipine in humans and is also the major photo-degradation product resulting from ultraviolet irradiation of nifedipine. Since irradiation by both visible and UV light result in products that promoted the same magnitude of uptake of Ga-67, multiple compounds resulting from the photo-degradation of nifedipine are believed to be effective in promoting the uptake of Ga-67.

EXAMPLE 5

The Nitroso-Derivative of Nifedipine Increases Gallium Uptake

The data in Example 3 indicate that the nitroso-derivative (FIG. 1) is one of the photo-degradation products that enhances gallium uptake, because the maximal uptake of Ga-67 was observed under conditions that correlate with the presence of the nitroso-derivative. Specifically, the nitroso-derivative predominates and is stable in fluorescent light, and the maximal activity of gallium uptake is observed and sustained under 4 hours of fluorescent irradiation of nifedipine. Moreover, the nitroso-derivative is only transiently produced by UV light (42), and continuous exposure of nifedipine to UV light for intervals longer than 1 hour results in progressive diminution of gallium uptake activity.

EXAMPLE 6

Gallium Uptake Unexpectedly Superior to Iron Transport

Photo-degraded nifedipine has been reported to increase the transferrin-independent uptake of $Fe^{2+}$ in nucleated rabbit erythrocytes. The nitroso-derivative of nifedipine was isolated and had the same pharmacological action as "crude" photo-degraded nifedipine in enhancing the uptake of $Fe^{2+}$ in these cells (44). However, the augmentation of uptake by photo-degraded nifedipine is much greater for Ga-67 (1,000-fold) than was reported for $Fe^{2+}$ (4-fold). Hence, gallium uptake is about 250 times greater than the reported increase in $Fe^{2+}$ uptake in the presence of nifedipine degradation products.

Photo-degraded nifedipine also fails to promote the uptake of iron in the trivalent state (44). Gallium is thought to exist in biological systems only in the trivalent form (45). Whether or not gallium and iron share the same system for transferrin-independent uptake, photo-degraded nifedipine appears to act as a much more effective ionophore for gallium than for iron.

EXAMPLE 7

Figure 2:
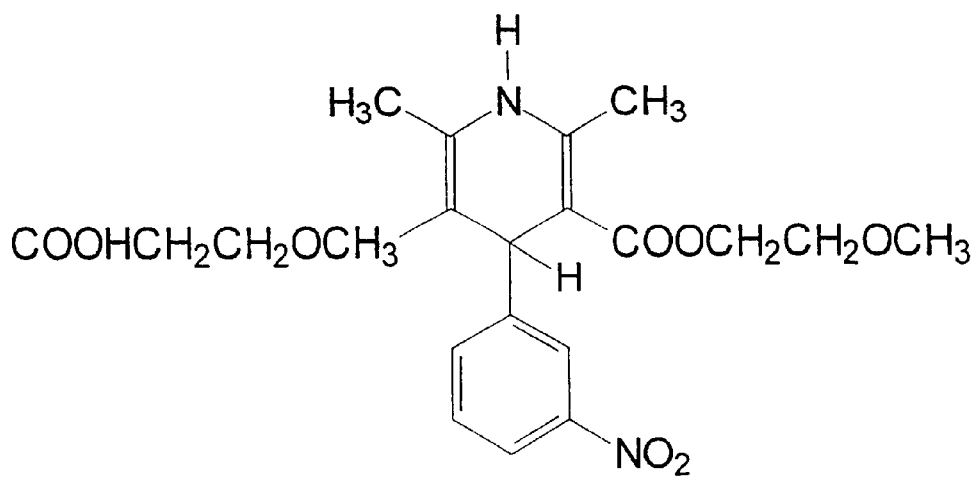
FIG. 2 shows the structural formula of the dihydropyridine calcium channel blocker, nimodipine.
Figure 3:
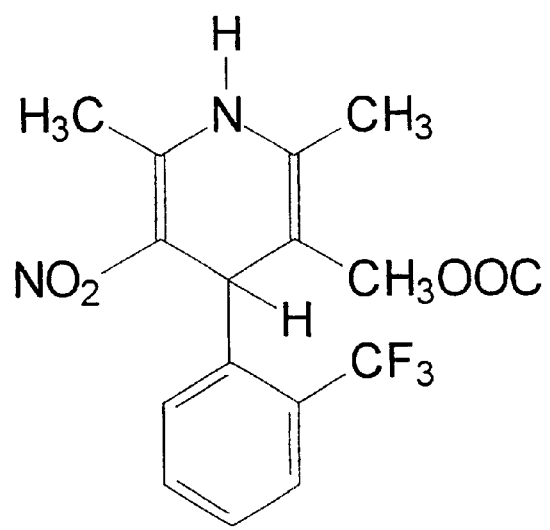
FIG. 3 shows the structural formula of the dihydropyridine calcium channel agonist, BAY K 8644.

Gallium Uptake Activity in Photo-degraded Structural and Functional Analogs of Nifedipine Using the methods explained in Examples 1–3, Ga-67 uptake in the presence of other calcium channel blockers and other dihydropyridines under both light-protected and photo-irradiated conditions was measured. Two non-dihydropyridine calcium channel blockers, diltiazem and verapamil, one dihydropyridine calcium channel blocker, nimodopine (FIG. 2), and one dihydropyridine calcium agonist, BAY K 8644 (FIG. 3), were tested. None of the light-protected or photo-irradiated compounds had an effect on Ga-67 uptake. Thus, neither calcium channel activity nor photo-irradiation of a dihydropyridine is predictive of gallium uptake activity. Nifedipine itself, if not irradiated, is also not active.

Comparison of the structures of the active nitroso-derivative (FIG. 1) and the inactive dihydropyridines, nimodipine (FIG. 2) and BAY K 8644 (FIG. 3), reveals that the position of the nitroso group and the fully aromatic ring system (in which both the pyridine and phenyl ring are aromatic) contribute to gallium uptake activity. For instance, the active nitroso-derivative (FIG. 1) has a nitroso group in the 2' position of the phenyl ring and a fully aromatic pyridine ring. Neither nimodipine (FIG. 2) nor BAY K 8644 (FIG. 3) has a fully aromatic phenylpyridine ring system. BAY K 8644 does not contain a nitroso group, and although nimodipine (FIG. 2) does have a nitroso group, it is in the 3' position on the phenyl ring.

Structures that are predicted to enhance gallium uptake include, but are not limited to, structures sterically similar to the active nitroso-derivative. These structures include, but are not limited to, nitrosophenyl-pyridines with the nitroso-group in the 2' or the 4' position of the phenyl ring, and substitutions of various alkyl, ester, and hydroxyl groups on both the pyridine and phenyl rings. Such substitutions include, but are not limited to: lower alkyls; carboxylic acids and esters of the formula COOR wherein R is an H or lower alkyl; $NO_2$, NO, or $SO_2$; or hydroxyls and ethers of the formula —OR, wherein R is an H or lower alkyl. In other embodiments, the two phenyl rings may be joined by 1 to 10 or more carbons, for example $(C=C-C)_n$, in either the cis or trans position, where n is 1–10, such as 5–10, or any number in between 1 and 10.

EXAMPLE 8

Photo-Degraded Nifedipine Increases Gallium Uptake by Tumor Cells

Nifedipine exposed to either visible or UV light markedly stimulates the transferrin-independent uptake of Ga-67 in cultured human, mouse, and rat tumor cells at relatively low concentrations (52). Using the methods described in Examples 1–3, several tumor cell lines were exposed to photo-degraded nifedipine (PDN) to measure gallium uptake. Tumor cells were obtained from the American Type Culture Collection (Manassas, Va.). A solution of 25 mM nifedipine was exposed to a strong fluorescent light source for 4 hours. The photo-degraded nifedipine was then incubated with tumor cells at a concentration of 25 $\mu$M for 30 minutes in the presence of Ga-67 citrate (PDN Ga-67 uptake). Control tumor cells were incubated in the absence of PDN in the presence of Ga-67 citrate for 30 minutes (Ga-67 uptake).

Mouse tumor cells tested included embryonic sarcoma (MMSV/3T3), myeloma (XS63), renal adenocarcinoma (RAG), testicular leydig cell tumor (I-10), T-cell lymphoma (RAW 8.1), and medullary thyroid carcinoma (MTC-M). Rat tumor cells tested included neuroblastoma (Neuro 2-A). Human tumor cells tested included melanoma (HT-144), colon adenocarcinoma (Caco-2), lung adenocarcinoma (Calu-1), and intraductal breast carcinoma (BT-474). Results from these experiments are shown in FIG. 4. Gallium uptake increased in all tumor cells tested.

EXAMPLE 9

Methods of Imaging and Treatment

Taking advantage of tumors relying to a greater degree on transferrin independent uptake of gallium than does normal tissues, the photo-degradation products of nifedipine can offer a method for selectively increasing the uptake of gallium by tumors. This finding is contrary to the accepted teaching that the photo-degradation products of nifedipine have historically been thought to lack pharmacological activity. However, the absence of other pharmacological activity indicates that the use of these compounds to increase gallium uptake is safe for clinical use. The absence of other pharmacological activity also indicates that the photo-degraded products of nifedipine can be dosed similarly to nifedipine, 0.5–2.0 mg/kg/day, but even larger doses can be used without adverse physiological consequences. Therapeutically effective doses of the gallium uptake enhancers of the present invention can be determined by one of skill in the art, with a goal of achieving tissue concentrations that are at least as high as that achieved with the administration of nifedipine.

The administration of nifedipine itself to subjects to increase the uptake of gallium is also included in the present invention, because the derivative produced by UV irradiation is also the primary metabolic product of nifedipine in humans, and the simultaneous presence of light shielded nifedipine does not reverse the effect of photo-degraded nifedipine. Using the assays described in this specification, it is possible to isolate individual photo-derivatives, or their analogs, and assess their ability to modulate the uptake of Ga-67. The effect of any such compound can also be readily assessed for efficacy as an imaging or anti-tumor agent, using the techniques described in the foregoing examples.

The method of this invention may also be used to improve tumor localization of other isotopes of gallium, such as Ga-68 or Ga-72 for local irradiation of tumors. The method of this invention may also be used to improve the uptake of stable gallium salts, such as gallium nitrate, gallium citrate, or gallium chloride, for the purpose of reducing bone resorption or as an adjunct to conventional chemotherapy.

EXAMPLE 10

Methods of Increasing Gallium Uptake for the Treatment of Tumors

The method includes administering the gallium uptake enhancers of the present invention, or a combination of the gallium uptake enhancers and one or more other chemotherapeutic anti-neoplastic pharmaceutical agents, including stable gallium, to the subject in a pharmaceutically compatible carrier, and in an amount effective to inhibit the development or progression of the tumor.

The vehicle in which the gallium uptake enhancers or chemotherapeutic agents are delivered can include pharmaceutically acceptable compositions of these substances, using methods well known to those with skill in the art. Any of the common carriers, such as sterile saline or glucose solution, can be utilized with the gallium uptake enhancers and chemotherapeutic agents of the invention. Routes of administration include but are not limited to oral and parenteral rountes, such as intravenous (iv), intraperitoneal (ip), rectal, topical, ophthalmic, nasal, sublingual, and transdermal.

The specific dose level and frequency of dosage for any particular subject may be varied, and will depend upon a variety of factors, including the activity of the specific compound, the metabolic stability and length of action of that compound, the age, body weight, general health, sex, diet, mode and time of administration, rate of excretion, drug combination, and severity of the condition of the host undergoing therapy. Determination of a specific dose can be determined by an attending physician, according to the condition of a subject, and the purpose for which the compound is being administered.

The present invention can be used in the treatment of a variety of tumors. Examples of such tumors include ovarian cancer, carcinoma of the urothelium, bladder cancer, bone metastases, colon cancer, lung cancer, thymoma, breast cancer, and lymphoma.

For example, VIG (vinblastine, ifosfamide, gallium nitrate) can be administered as an anti-tumor treatment (53, 54) for ovarian cancer and advanced carcinoma of the urothelium. Vinblastine, 0.08–0.11 mg/kg, is administered iv on days 1 and 2, ifosfamide, 0.9–1.2 $g/m^2$ iv, on days 1–5 with mesna uroprotection, gallium nitrate, 225–300 $mg/m^2$/day, as a continuous infusion for 120 hours or days 1–5, and G-CSF. Cycles are repeated at 21-day intervals. Gallium uptake enhancers can be added to these regimens to improve the tumor response.

Combination therapy with paclitaxel, G-CSF (filgrastim), gallium nitrate, and calcitriol can be administered as an anti-tumor treatment (55), for example colon cancer adenocarcinoma or thymoma. Gallium nitrate, 300 $mg/m^2$/day, is administered as a continuous iv infusion for 120 hours. For the last 24 hours of gallium administration, paclitaxel, 90–225 mg/m$^2$, is administered as a continuous iv infusion for 24 hours. Calcitriol, 0.5 μg/day orally is administered on days 1–7. G-CSF, 5 μg/kg/day, can be added to the regimen for higher doses of paclitaxel. The cycle is repeated every 21 days. Gallium uptake enhancers can be added to these regimens to improve the tumor response.

Gallium nitrate, 200–350 mg/m$^2$/day continuous iv infusion for 7 days in combination with hydroxyurea, 500–1000 mg/day orally can be used as an anti-neoplastic regimen (56), for example with non-Hodgkin's lymphoma. Gallium uptake enhancers can be added to this regimen to improve the tumor response.

Another anti-tumor combination therapy comprises cisplatin, etoposide, and gallium chloride (57), for example for small cell and non-small cell lung cancers. Cisplatin and etoposide are administered as a continuous iv infusion over 5 days. Gallium chloride, 400 mg/day, is given orally. The cycles can be repeated every 21 days and 6 or more cycles can be given.

The combination therapies are of course not limited to the lists provided in these examples, but include any composition for the treatment of tumors.

The present invention can also be used in the treatment of a variety of hematological malignancies by local radiotherapy (47, 48, 49, 50, 51, 58). Examples of such hematological malignancies include non-Hodgkin's lymphoma, Hodgkin's lymphoma, and leukemia.

For example in the treatment of acute lymphoblastic leukemia (ALL) and acute myelogenous leukemia (AML), a radioactive isotope of gallium, such as Ga-67 citrate, is administered at a dose of about 36–105 mCi, iv push, for about 12 doses. Gallium uptake enhancers in accordance with the present invention can be administered to improve the tumor response to this therapy. Additionally, chemotherapeutic agents such as hydroxyurea, 1-beta-D-arabinofuranosylcytosine, and methotrexate can be added to this regimen to further improve the tumor response to this therapy (58).

Gallium uptake enhancers can be administered locally to treat cutaneous tumors. For example, nifedipine is delivered locally to the tumor and absorbed transdermally (63, 64, 65). The nifedipine is then photo-irradiated, allowing the production and transdermal absorption of the gallium uptake enhancers, and increasing the uptake of gallium by the tumor cells.

EXAMPLE 11

Gallium Uptake Enhancers for the Imaging of Tumors

The present invention improves the uptake of gallium in tumors (such as hepatomas and lymphomas) that already exhibit good gallium uptake, and enhances gallium uptake in tumors that previously have had poor gallium uptake. The present invention enhances the uptake of isotopes of gallium to improve gamma ray emission detection (gallium scan) or positron emission detection (PET scan) (59). This uptake enhancement allows the normal time delay between injection and imaging of Ga-67 to be substantially reduced (for example from the normal 72 hour delay, to 24–36 hours or even less). This technique also improves the target:background ratio of activity between tumors (or other abnormal structures for which gallium uptake is enhanced) and the normal background tissues. This gallium uptake enhancers also can reduce the dose of gallium necessary to image by as much or even more than one-half the amount necessary to perform the gallium scan in the absence of a gallium uptake enhancer.

EXAMPLE 12

Gallium Uptake Enhancers for Reducing Bone Resorption

Stable gallium, including gallium nitrate, can be used in the treatment of bone-resorptive diseases such as Paget's disease, osteoporosis, hypercalcemia of malignancy, multiple myeloma, blastic bone metastasis, and lytic bone metastasis (60, 61, 62). Bone treated with gallium is significantly more resistant to cell-mediated osteolysis by osteoclasts, and bone lysis induced by parathyroid hormone and tumor necrosis factor (60). Gallium uptake enhancers can be administered with gallium, such as stable gallium, for the treatment of bone-resorptive diseases.

The hypercalcemia of malignancy can be treated by administering gallium nitrate by continuous i.v. infusion at doses of 100–200 mg/m$^2$ for 5–7 days to achieve normocalcemia (60). This is approximately one-third of the dose used as an anti-tumor agent. Gallium uptake enhancers can be added to this regimen to reduce the dose and duration of gallium therapy necessary to achieve normocalcemia, or to increase the speed and efficacy of the therapy.

Both lytic and blastic bone metastasis (for example metastatic prostatic adenocarcinoma) can be treated by administering gallium nitrate by continuous iv infusion 200 mg/m$^2$ for 5 days (60). A low dose regimen of 40 mg/day by subcutaneous injection, 2 weeks on/2 weeks off for 6 months can also be used. Gallium uptake enhancers can be added to this regimen to increase the efficacy of the gallium therapy or to reduce the dose and duration of gallium therapy necessary to achieve a therapeutic effect.

Paget's disease can be treated by administering gallium nitrate 100 mg/m$^2$/day continuous iv infusion for 5 days (61). Gallium uptake enhancers can be added to this regimen to increase the efficacy of the gallium therapy, or to reduce the dose and duration of gallium therapy necessary to achieve a therapeutic effect.

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

REFERENCES

1. Edwards C L et al. J Nucl Med 10: 103–105, 1969.
2. Halpern S et al. Nuclear Medicine Annual 1980. Raven Press, New York, 1980.
3. Beckerman C et al. Sem Nucl Med 15: 72–103, 1985.
4. Israel O et al. J. Nucl. Med. 31: 365–368, 1990.
5. Kaplan W D. J. Nucl. Med. 31: 369–371, 1990.
6. Andrews G A et al. Radiology 61: 570–588, 1953.
7. Chitambar C R et al. Cancer Research 54: 3224–3228, 1994.
8. Seligman P A et al. Blood 82: 1608–1617, 1993.
9. Chitambar C R et al. Am J Clin Oncol 20: 173–178, 1997.
10. Tzen K Y et al. J Nucl Med 5: 327–332, 1980.
11. Tsan, M F. J. Nucl. Med. 26: 89–92, 1985.
12. Merz T et al. Cancer Res. 34: 2495–2499, 1974.
13. Anghileri L J et al. Oncoogy 34: 74–77, 1977.
14. Hoffer, P. J. Nucl. Med. 21: 282–285, 1990.
15. Harris A W et al. Cancer Res 37: 3635–3638, 1977.
16. Larson S M et al. J. Nucl. Med. 20: 837–842, 1979.
17. Chitambar C R et al. Blood 80: 505–511, 1992.
18. Otten J et al. Proc. Soc. Exptl. Biol. Med. 142: 92–95, 1973.

19. Wong, H et al. Int. J. Nucl. Med. Biol. 7: 9–16, 1980.
20. Vallabhajosula S R et al. Eur. J. Nucl. Med. 7: 462–468, 1982.
21. Harris W R et al. Biochemistry 22: 292–299, 1983.
22. Tsan M E et al. Int. J. Nucl. Med. Biol. 7: 270–273, 1980.
23. Gupta A D et al. Hematol Pathol 4: 37–41, 1990.
24. Sciot R. et al. Histopathology 16: 59–62, 1990.
25. Chen, D C P et al. Eur. J. Nucl. Med. 7: 536–540, 1982.
26. Bradley, W P et al. J. Nucl. Med. 20: 243–247, 1979.
27. Oster, Z H et al. J. Nucl. Med. 18: 356–358, 1976.
28. Hayes, R L et al. J. Nucl. Med. 12: 437–438, 1971(abs)
29. Sohn M H et al. J Nucl Med 34: 2135–2143, 1993.
30. Basset P et al. Cancer Res 46: 1644–1647, 1986.
31. Craven C M et al. Proc Natl Acad Sci USA 84: 3457–3461, 1987.
32. Taetle R et al. J. Clin Invest 75: 1061–1067, 1985.
33. Brissot P et al. J Clin Invest 76: 1463–1470, 1985.
34. Sturrock A et al. J Biol Chem 265: 3139–3145, 1990.
35. Kaplan J et al. J Biol Chem 266: 2997–3004, 1991.
36. Chitambar C R et al. Cancer Res. 47: 3929–3934, 1987.
37. Luttropp C A et al. J Nucl Med. 39: 1405–1411, 1998.
38. Phelouzat M A et al. Biochem J. 305: 133–137, 1995.
39. Smith P K et al. Anal. Biochem. 150: 76–85, 1985.
40. Berson J A, et al. J Am Chem Soc 77: 447–450, 1955.
41. Majeed I A et al. J Pharm Pharmacol 39: 1044–1046, 1987.
42. Hayase N et al. J Pharm Sci 83: 532–538, 1994.
43. Grundy J S et al. J Pharm and Biomed Anal 12: 1529–1535, 1994.
44. Savigni D L et al. Biochem Pharmacol 51: 1701–1709, 1996.
45. Perkinson J D et al. Radiology 61: 543–550, 1953.
46. Franckowlak G et al. Europ J Pharmacol 114: 223–226, 1985.
47. Van Leeuwen-Stok, E A et al. Leuk Lymphoma 31: 533–44, 1998.
48. Van Leeuwen-Stok, E A et al. Int J Radiat Oncol Biol Phys 35: 507–17, 1996.
49. Jonkhoff, A R et al. Leuk Res 19: 169–74, 1995.
50. Jonkhoff, A R et al. Br J Cancer 72: 1541–6, 1995.
51. Jonkhoff, A R et al. Br J Cancer 67: 693–700, 1993.
52. Luttropp, C A et al. J Nucl Med 40: 159–165, 1999.
53. Dreicer R et al. Cancer 79: 110–4, 1997.
54. Dreicer R et al. Am J Clin Oncol 21: 287–290, 1998.
55. Sandler, A et al. Am J Clin Oncol 21: 180–4, 1998.
56. Chitambar, C R et al. Am J Clin Oncol 20: 173–8, 1997.
57. Collery, P et al. Anticancer Res 11: 1529–32, 1991.
58. Jonkhoff, A R et al. Br J Cancer 72: 1541–6, 1995.
59. Draisma, A et al. Tumori 84: 434–41, 1998.
60. Warrell, R P. Cancer 80: 1680–5, 1997.
61. Matkovic, V et al. Lancet 335: 72–5, 1990.
62. Montouri, E et al. Medicina (B Aires) 53: 65–76, 1993.
63. Kobayashi, D et al. Biol Pharm Bull 16: 254–8, 1993.
64. Diez, I et al. J Pharm Sci 80: 931–4, 1991.
65. Kondo, S et al. J Pharmacobiodyn 10: 662–8, 1987.

We claim:

1. A method of increasing gallium uptake by a cell, comprising:
exposing the cell to an effective amount of a gallium uptake enhancer comprising a nifedipine photodegradation product, or an analog thereof, that promotes gallium uptake by the cell.

2. The method of claim 1, further comprising exposing the cells to gallium.

3. The method of claim 2, wherein the gallium is a gallium compound, salt, or a gallium isotope.

4. The method of claim 3, wherein the gallium compound is selected from the group consisting of gallium nitrate, gallium citrate and gallium chloride.

5. The method of claim 3, wherein the gallium isotope is selected from the group consisting of Ga-67, Ga-68, Ga-69, Ga-71 and Ga-72.

6. The method of claim 2, wherein the cell is a tumor cell, and the method further comprises administering one or more chemotherapeutic anti-neoplastic pharmaceutical agents selected from the group consisting of vinblastine, ifosfamide, hydroxyurea, paclitaxel, cisplatin, methotrexate, 1-beta-D-arabinofuranosylcytosine, and etoposide.

7. The method of claim 2, wherein the cell is a tumor cell selected from the group consisting of a sarcoma, myeloma, renal adenocarcinoma, testicular leydig cell tumor, medullary thyroid carcinoma, neuroblastoma, melanoma, colon adenocarcinoma, lung adenocarcinoma, or intraductal breast carcinoma.

8. The method of claim 2, wherein the cell is a bone cell.

9. The method of claim 2, wherein the cell is exposed to the gallium and the gallium uptake enhancer by administering the gallium and gallium uptake enhancer to a subject.

10. The method of claim 9, wherein the subject has a tumor, and the gallium in administered in a therapeutically effective antineoplastic amount, when combined with the gallium uptake enhancer.

11. The method of claim 9, wherein the subject has a tumor, and the gallium is administered in an amount effective to image the tumor in a gallium scan, when the gallium is administered in combination with the gallium uptake enhancer.

12. The method of claim 1, wherein the gallium uptake enhancer is a transferrin independent gallium uptake enhancer.

13. The method of claim 1, wherein the gallium uptake enhancer is a nitrosophenylpyridine.

14. The method of claim 13, wherein the nitrosophenylpyridine is a 2'- or 4'-nitrosophenylpyridine derivative.

15. The method of claim 13, wherein the nitrophenylpyridine is 2'-nitrosophenylpyridine derivative.

16. The method of claim 1, wherein the gallium uptake enhancer is selected from the group consisting of:

A-B and

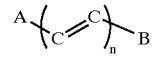

wherein A is a pyridine and B is a nitrosophenyl, and n=1–10.

17. The method of claim 16, wherein B is a 2'-nitrosophenyl or 4'-nitrosophenyl.

18. The method of claim 17, wherein the gallium uptake enhancer is:

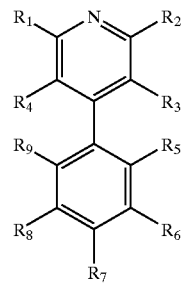

wherein
$R_{1-4}$, $R_6$, and $R_{8-9}$ are independently selected from the group consisting of H, halogen, haloalkyl, $NO_2$, NO, $SO_2$, a C1-6 alkyl, a $COOR_{10}$ wherein $R_{10}$ is H or C1-6 alkyl, and an $—OR_{11}$ wherein $R_{11}$ is H or C1-6 alkyl;

and $R_5$ and $R_7$ are independently selected from the group consisting of H, halogen, haloalkyl, $NO_2$, NO, $SO_2$, a C1-6 alkyl, a $COOR_{10}$ wherein $R_{10}$ is H or C1-6 alkyl, and an $—OR_{11}$ wherein $R_{11}$ is H or C1-6 alkyl, wherein at least one of $R_5$ and $R_7$ is NO.

19. The method of claim 18, wherein $R_{1-4}$, $R_6$, and $R_{8-9}$ are independently selected from the group consisting of C1-6 alkyl, a $COOR_{10}$ wherein $R_{10}$ is H or C1-6 alkyl, and $—OR_{11}$ wherein $R_{11}$ is H or C1-6 alkyl.

20. The method of claim 18, wherein $R_5$ is NO and $R_7$ is H.

21. The method of claim 20, wherein $R_1=R_2=CH_3$, $R_3=R_4=COOCH_3$.

22. The method of claim 21, wherein $R_6=R_8=R_9=H$.

23. The method of claim 1, wherein the gallium uptake enhancer is selected from the group consisting of:

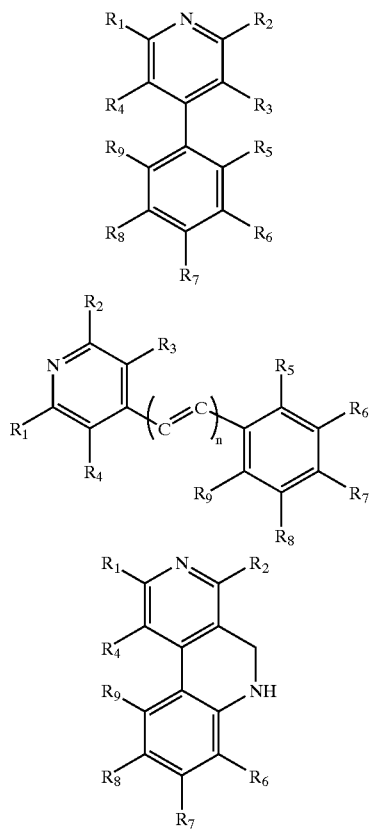

wherein n=1–10, and wherein $R_{1-4}$, $R_6$, and $R_{8-9}$ are independently selected from the group consisting of H, halogen, haloalkyl, $NO_2$, NO, $SO_2$, a C1-6 alkyl, a $COOR_{10}$ wherein $R_{10}$ is H or C1-6 alkyl, and an $—OR_{11}$ wherein $R_{11}$ is H or C1-6 alkyl;

and $R_5$ and $R_7$ are independently selected from the group consisting of H, halogen, haloalkyl, $NO_2$, NO, $SO_2$, a C1-6 alkyl, a $COOR_{10}$ wherein $R_{10}$ is H or C1-6 alkyl, and an $—OR_{11}$ wherein $R_{11}$ is H or C1-6 alkyl, wherein at least one of $R_5$ and $R_7$ is NO.

24. A method of imaging a tumor with a gallium scan, comprising:

administering an effective amount of a gallium uptake enhancer comprising a nifedipine photodegradation product, or an analog thereof, that increases uptake of gallium by a tumor; and administering a sufficient amount of gallium to perform the gallium scan, wherein the sufficient amount of gallium is less than required to perform the gallium scan in an absence of the gallium uptake enhancer.

25. The method of claim 24, wherein the gallium uptake enhancer is a transferrin independent gallium uptake enhancer.

26. The method of claim 25, wherein the gallium uptake enhancer is a 2'-nitrosophenylpyridine.

27. The method of claim 24, wherein the nifedipine photodegradation product or analog is selected from the group consisting of:

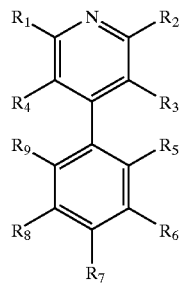

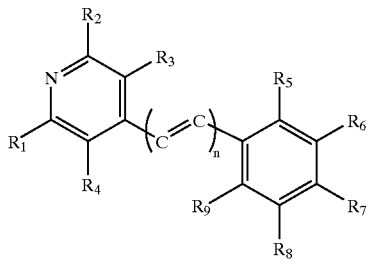

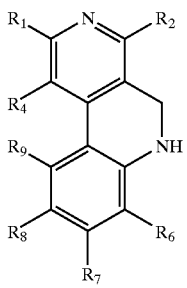

wherein n=1–10, and wherein $R_{1-4}$, $R_6$, and $R_{8-9}$ are independently selected from the group consisting of H, halogen, haloalkyl, $NO_2$, NO, $SO_2$, a C1-6 alkyl, a $COOR_{10}$ wherein $R_{10}$ is H or C1-6 alkyl, and an $—OR_{11}$ wherein $R_{11}$ is H or C1-6 alkyl;

and $R_5$ and $R_7$ are independently selected from the group consisting of H, halogen, haloalkyl, $NO_2$, NO, $SO_2$, a C1-6 alkyl, a $COOR_{10}$ wherein $R_{10}$ is H or C1-6 alkyl, and an $—OR_{11}$ wherein $R_{11}$ is H or C1-6 alkyl, wherein at least one of $R_5$ and $R_7$ is NO.

28. The method of claim 27, wherein the nifedipine photodegradation product or analog is:

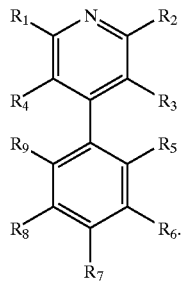

29. The method of claim 24, wherein administering the gallium comprises administering Ga-67.

30. The method of claim 29, wherein the effective amount of gallium is less than one-half an amount of gallium required to perform the gallium scan in the absence of the gallium uptake enhancer.

31. The method of claim 29, wherein administering the gallium comprises administering no more than about 5 millicuries of the Ga-67.

32. The method of claim 24, wherein the tumor is selected from the group consisting of a sarcoma, myeloma, renal adenocarcinoma, testicular leydig cell tumor, medullary thyroid carcinoma, neuroblastoma, melanoma, colon adenocarcinoma, lung adenocarcinoma, or intraductal breast carcinoma.

33. The method of claim 29, wherein administering the gallium uptake enhancer allows imaging of the tumor at 24 hours or less after administration of the gallium.

34. The method of claim 24, wherein administering an effective amount of gallium comprises administering about 0.5 to about 2.0 mg/kg/day of the nifedipine photodegradation product.

35. The method of claim 34, wherein the nifedipine photodegradation product is a 2'-nitrosophenylpyridine.

36. The method of claim 10, wherein the tumor is a cutaneous tumor, and the gallium uptake enhancer is nifedipine applied to skin in an area of the cutaneous tumor, which area is subsequently irradiated with light that produces the nifedipine photodegradation product gallium uptake enhancer.

37. The method of claim 10, wherein the gallium uptake enhancer is administered systemically to a subject having a tumor, within an effective period of time as a gallium containing chemotherapeutic agent to increase uptake of the chemotherapeutic agent into the tumor.

38. The method of claim 37, wherein the gallium uptake enhancer is administered orally to the subject.

39. A method of treating a cutaneous tumor, comprising:
    administering nifedipine to the subject;
    photoirradiating the cutaneous tumor with light that causes the nifedipine to form a photodegradation product that enhances gallium uptake;
    administering gallium to the subject.

40. The method of claim 39, wherein the nifedipine is administered systemically.

41. The method of claim 39, wherein the nifedipine is applied topically to the cutaneous tumor.

42. A method of screening for a gallium uptake enhancer, comprising:
    exposing cells to a test agent comprising a nifedipine photodegradation product, or an analog thereof, in the presence of gallium;
    measuring an uptake of gallium in the cell, and determining if the uptake of gallium is greater or less than in the absence of the test agent.

43. The method of claim 42, wherein the cells are cultured Chinese Hamster Ovary cells.

44. The method of claim 42, wherein the cells are transferrin receptor negative cells.

45. A gallium uptake enhancer detected by the method of claim 42.

46. The method of claim 1, wherein the nifedipine photodegradation product is not produced by photo-irradiation.

47. The method of claim 46, wherein the nifedipine photodegradation product is made by chemical synthesis.

48. A method of increasing gallium uptake by a cell in a subject, comprising:
    administering to the subject an effective amount of a compound that increases gallium uptake, the compound comprising:

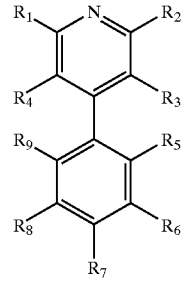

wherein $R_{1-4}$, $R_6$, and $R_{8-9}$ are independently selected from the group consisting of H, halogen, haloalkyl, $NO_2$, NO, $SO_2$, a C1-6 alkyl, a $COOR_{10}$ wherein $R_{10}$ is H or C1-6 alkyl, and an —$OR_{11}$ wherein $R_{11}$ is H or C1-6 alkyl; and $R_5$ and $R_7$ are independently selected from the group consisting of H, halogen, haloalkyl, $NO_2$, NO, $SO_2$, a C1-6 alkyl, a $COOR_{10}$ wherein $R_{10}$ is H or C1-6 alkyl, and an —$OR_{11}$ wherein $R_{11}$ is H or C1-6 alkyl, wherein at least one of $R_5$ and $R_7$ is NO.

49. The method of claim 48, wherein the method is a method of increasing gallium uptake in a tumor cell of the subject.

50. The method of claim 48, wherein the compound is a 2'- or 4'-nitrosophenylpyridine derivative.

51. The method of claim 50, wherein the compound is the 2' nitrosophenylpyridine derivative.

* * * * *

UNITED STATES PATENT AND TRADEMARK OFFICE
CERTIFICATE OF CORRECTION

PATENT NO. : 6,558,650 B1
DATED : May 6, 2003
INVENTOR(S) : Morton et al.

It is certified that error appears in the above-identified patent and that said Letters Patent is hereby corrected as shown below:

Column 1,
Line 56, "for" should read -- or --.

Column 4,
Line 59, "GA-69" should read -- Ga-69 --.

Column 6,
Line 1, "$CCl_2$" should read -- $CCl_3$ --.

Column 12,
Line 62, "25 $\mu$m" should read -- 25 mM --.

Column 13,
Line 24, "25 $\mu$m" should read -- 25 mM --.

Column 21,
Line 14, "$R_1=R_2=CH_3$" should read -- $R_1=R_2=H$ --.

Signed and Sealed this

Second Day of December, 2003

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 6,558,650 B1 | Page 1 of 1 |
| APPLICATION NO. | : 09/647954 | |
| DATED | : May 6, 2003 | |
| INVENTOR(S) | : Morton et al. | |

It is certified that error appears in the above-identified patent and that said Letters Patent is hereby corrected as shown below:

Column 1, following line 11, insert new paragraph to read as follows:

STATEMENT OF GOVERNMENT SUPPORT

This invention was made with United States government support pursuant to Grant No. CA77574, from the National Institutes of Health; The United States government has certain rights in the invention.

Signed and Sealed this

Second Day of December, 2008

JON W. DUDAS
*Director of the United States Patent and Trademark Office*